US00PP27890P3

(12) United States Plant Patent
Randag

(10) Patent No.: US PP27,890 P3
(45) Date of Patent: Apr. 11, 2017

(54) CALLA LILY PLANT NAMED 'GRAN PARADISO'

(50) Latin Name: *Zantedeschia sprengeri*
Varietal Denomination: Gran Paradiso

(71) Applicant: Sande B.V., 't Zand (NL)

(72) Inventor: Cecilius Jan-Jochem Randag, 't Zand (NL)

(73) Assignee: Sande B.V., 't Zand (NL)

( * ) Notice: Subject to any disclaimer, the term of this patent is extended or adjusted under 35 U.S.C. 154(b) by 85 days.

(21) Appl. No.: 14/544,487

(22) Filed: Jan. 12, 2015

(65) Prior Publication Data

US 2015/0296694 P1 Oct. 15, 2015

Related U.S. Application Data

(60) Provisional application No. 61/964,771, filed on Apr. 11, 2014.

(51) Int. Cl.
*A01H 5/02* (2006.01)

(52) U.S. Cl.
USPC ..... Plt./490

(58) Field of Classification Search
USPC ..... Plt./490
See application file for complete search history.

(56) References Cited

PUBLICATIONS

UPOV—International Union for the Protection of New Varieties of Plants: PLUTO Plant Variety Database; Jun. 11, 2016; cultivar name—'Gran Paradiso' (1 pg).*

* cited by examiner

*Primary Examiner* — Susan McCormick Ewoldt
(74) *Attorney, Agent, or Firm* — The Webb Law Firm

(57) ABSTRACT

'Gran Paradiso' is a new variety of calla lily having flowers with an Orange Red-colored spathe that produces 3-10 flowers per tuber. The flower stems are about 90 cm. in height and the leaves are green with whitish spots and have a leathery texture.

2 Drawing Sheets

Botanical classification: *Zantedeschia sprengeri*.
Varietal denomination: 'GRAN PARADISO'.

BACKGROUND OF THE NEW PLANT

The present invention comprises a new and distinct cultivar of calla lily, botanically known as *Zantedeschia sprengeri* and hereinafter referred to by the cultivar name 'Gran Paradiso'.

'Gran Paradiso' is a product of a planned breeding program which had the objective of creating *Zantedeschia* hybrids for cut flower production in a wide range of colors with a large, classic flower shape. The breeding program began in 1989 and the new cultivar is a seedling selected from the crossing of *Zantedeschia sprengeri* seedling Z030624 (female parent, unpatented) with *Zantedeschia sprengeri* variety 'Treasure' (male parent, unpatented). 'Gran Paradiso' was selected in 2008 by the inventor C. J. J. Randag in 't Zand, The Netherlands as one flowering plant within the progeny of the stated cross.

The first act of asexual reproduction of 'Gran Paradiso' by tissue culture was performed by the inventor in August of 2008 in 't Zand, The Netherlands. Further asexual reproductions by tissue culture at the same location has demonstrated that the combination of characteristics as herein disclosed for the new cultivar are retained and reproduced true to type through successive generations of asexual reproduction.

The following observations, measurements and comparisons describe plants at 12-14 weeks after planting grown in 't Zand, The Netherlands under greenhouse conditions which approximate those generally used in horticultural practice. Color references are made to The 2001 R.H.S. Colour Chart of The Royal Horticultural Society of London, except where general color terms of ordinary significance are used.

The present invention has not been evaluated under all possible environmental conditions. The phenotype may vary with variation in environment without a change in the genotype of the plant.

The following traits have been repeatedly observed and determined to basic characteristics of 'Gran Paradiso' which, in combination, distinguish this calla lily as a new and distinct cultivar:

1. Orange red-colored spathe;
2. Big spathe size
3. Tall flower stems and
4. High flower production.

Further, when compared to calla lily plant named 'Tresor' (unpatented), the upper surface spathe color of 'Tresor' is Red Group RHS 46A and the lower surface spathe color of 'Tresor' varies between Yellow Group RHS 13B to 14A, while the upper surface spathe color of 'Gran Paradiso' varies between Orange Group RHS 25A to 25D and the lower surface spathe color varies between Yellow-Green Group RHS 144A and 144B. Further, 'Gran Paradiso' exhibits larger and more numerous leaf maculation spots than 'Tresor'.

Table 1 provides similarities and differences of 'Gran Paradiso' to its parents Z030624 and Treasure

TABLE 1

| 'Gran Paradiso' | Similarities | Differences |
|---|---|---|
| Z030624 | Leaf shape | Number of inflorescences (3-7) |
| | Spathe color | No spots on leaves |
| 'Treasure' | Leaf shape | Number of inflorescences (1-5) |
| | | Spathe shape (Funnel) |

BRIEF DESCRIPTION OF THE DRAWINGS

The accompanying photographic drawings illustrate the new variety at 12-14 weeks after planting, with the colors being as nearly true as is possible with color illustrations of this type.

DESCRIPTION OF THE PLANT

THE PLANT

Figure 1:
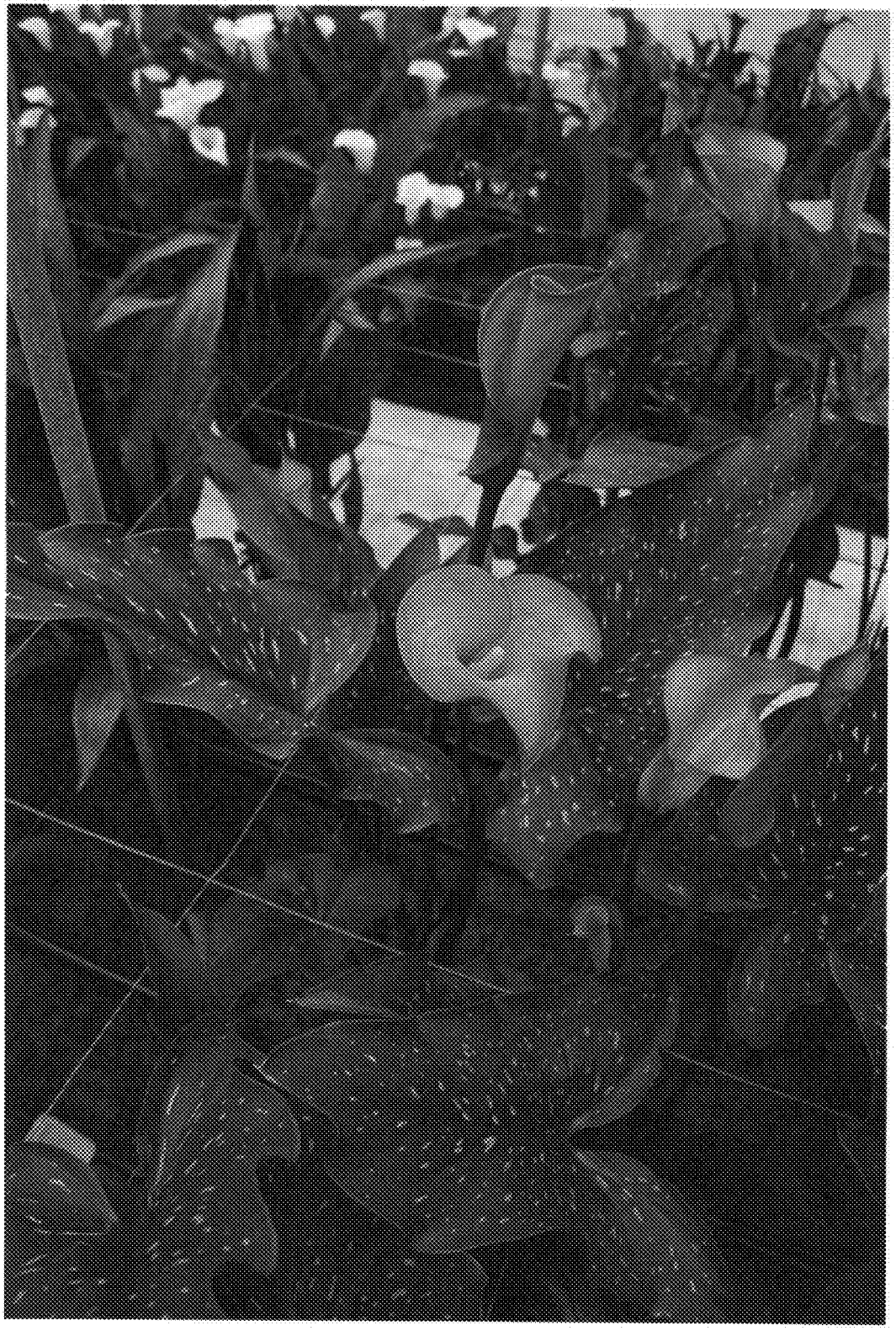
FIG. 1 Single plant of Gran Paradiso.
Figure 2:
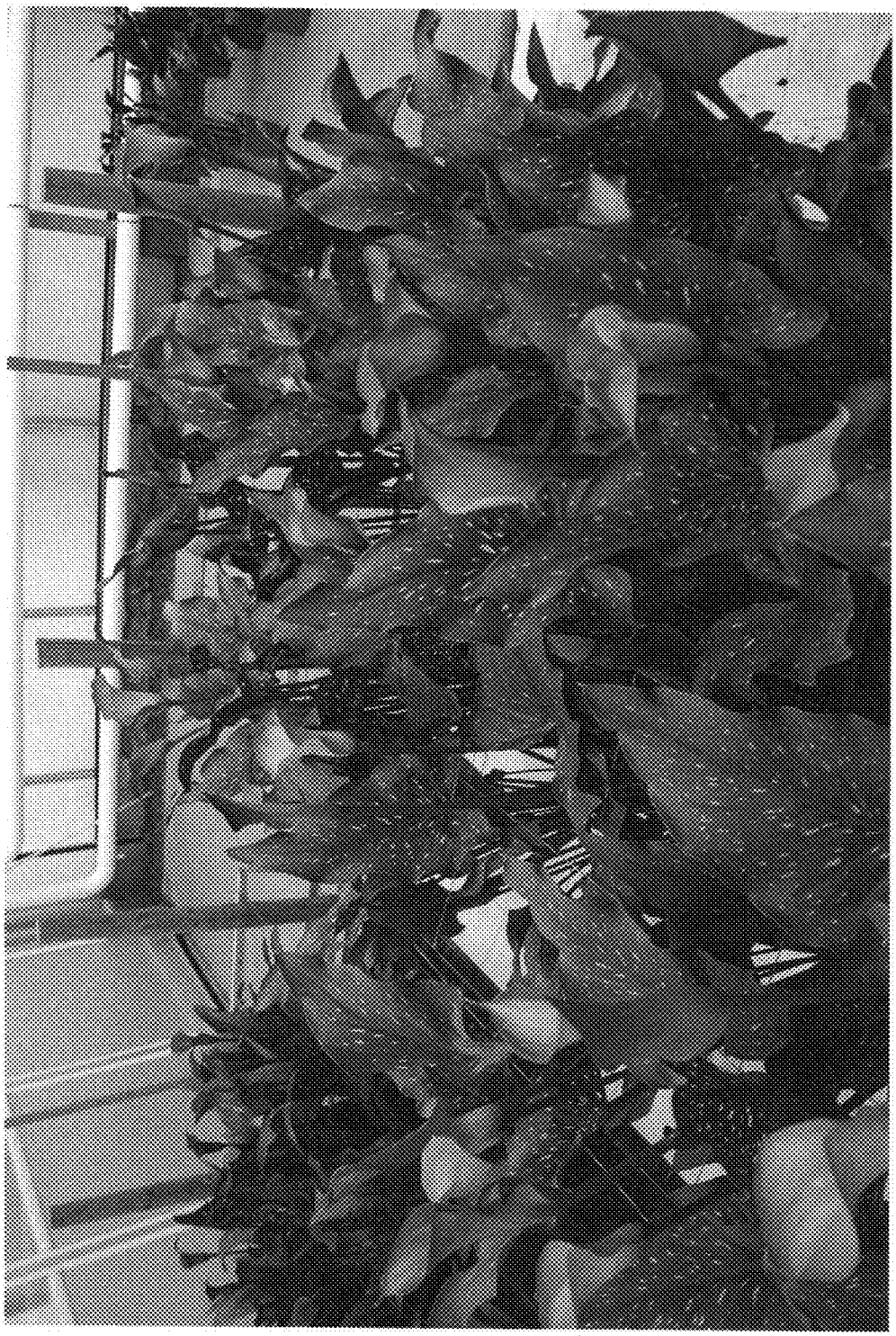
FIG. 2 Group of plants of Gran Paradiso.

Size:

*Height of the leaf canopy above the soil.*—25-95 cm.

*Height of top of flower above the soil.*—50-100 cm.

*Diameter.*—25-60 cm.

Form: Erect.

Number of flowers per tuber:

*Size* 14-16 cm. *in diameter.*—3-6 flowers.

*Size* 16-18 cm *in diameter.*—5-8 flowers.

*Size* 18-20 cm. *in diameter.*—6-10 flowers.

Branches:

*Character.*—From 2-7 and like the variety 'Picasso' (U.S. Plant Pat. No. 15,282).

*Color.*—Between RHS 147A and 147B.

Leaves:

*Size.*—Width: 5-25 cm. Length: 7-30 cm.

*Number per plant.*—7-20.

*Shape.*—Sagittate.

*Color.*—Upper surface: Green Group RHS 137A to 137B, with transparent White Group RHS 155C and N155A spots. Lower surface: Green Group RHS 138A to 138B, with transparent White Group RHS 155C and N155A spots.

*Apex.*—Acute.

*Base.*—Hastate.

*Margin.*—Undulate, having a color between RHS 137 A to 137 B.

*Veins.*—Configuration: Pinnate. Color: Between RHS 138 A-138 B.

*Surface quality.*—Leathery.

*Petiole.*—Length: 20-70 cm. Diameter: 12 mm. Color: The base is White Group RHS 155A and the upper part of the petiole is between RHS 138A and 138B.

Roots:

*Color.*—White.

*Branching.*—Similar to other *Zantedeschia* varieties.

THE FLOWER AND SEEDS

Spathe:

*Size.*—Length (measured from opening to tip): 4.5-10 cm. Width: 3-8 cm. Height 7-14 cm.

*Color.*—Upper surface: Varies between RHS 25A and 25D. Lower surface: Varies between RHS 144A and 144B.

*Vein color.*—Varies between RHS N34A and N34B.

*Shape.*—Cupped.

*Apex.*—Acute.

*Base.*—Acute.

*Texture.*—Smooth (upper and lower surfaces).

Spadix:

*Size.*—Length: 30-70 mm. Diameter: 3-13 mm.

*Color.*—Between RHS 23A and 23B.

*Position relative to spathe.*—Upright.

Peduncle:

*Size.*—Length: 40-90 cm. Diameter: 3-18 mm.

*Color.*—Upper part varies between RHS 137A and 137B and the lower part is RHS 157C.

*Texture.*—Smooth.

Reproductive organs:

*Location of female organs.*—Basal position of the spadix.

*Location of male organs.*—Upper position of the spadix.

*Perianth.*—Conspicuous.

*Stamens.*—Presence: Not visible before pollen release. Number: More than 50. Pollen amount: Abundant and similar to 'Picasso' (U.S. Plant Pat. No. 15,282), but not quantifiable due to minute pollen size. Color: Between White Group RHS 155A and 155B.

*Anther.*—Shape: Round and wire-like. Length: Less than 1 mm. Color: Between RHS 23A and 23B.

*Filament.*—Length: Less than 1 mm. Color: Between White Group RHS 155A and 155B.

*Pistil.*—Number: 30 to 50. Length beyond perianth: About 1 mm.

*Stigma.*—Shape: Round. Size: Less than 1 mm.

*Style.*—Length: Less than 1 mm. Color: Between RHS 15A and 15B.

*Ovaries.*—Texture: Smooth. Length: Between 1 to 10 mm. Width: Between 1 to 10 mm. Color: Top color varies between RHS 140B and N34A, bottom color varies between RHS 155B and 157C.

Seeds:

*Length.*—4-7 mm.

*Width.*—3-6 mm.

*Color.*—Between Yellow-Green Group RHS 150A and 151A.

*Amount.*—Between 1-100.

Fruit:

*Amount.*—Multiple berries produced.

*Shape.*—Irregular.

*Color.*—Exhibits a main color of Yellow-Green Group RHS 144A to 144C with a dot located around the stigma of variable intensity of Red-Purple Group RHS 59A to 60C.

GENERAL

Disease resistance: No unusual susceptibility to diseases noticed to date.

Pest resistance: No unusual susceptibility to pests noticed to date.

Heat tolerance: No heat tolerance.

Hardiness: Not hardy.

Flowering: Tubers planted in a greenhouse in The Netherlands in February produce flowers in April. Tubers planted outdoors in The Netherlands in May produce flowers in July. In general, the time from planting to first flowering takes eight weeks. However, tubers stored for a longer period before planting may flower earlier — up to five weeks after planting.

Lastingness: About two weeks on the plant.

Fragrance: None.

I claim:

1. A new and distinct variety of calla lily plant named 'Gran Paradiso' as herein described and illustrated.

* * * * *